United States Patent [19]

Volkwein

[11] Patent Number: 5,424,195
[45] Date of Patent: Jun. 13, 1995

[54] METHOD FOR IN SITU BIOLOGICAL CONVERSION OF COAL TO METHANE

[75] Inventor: Jon C. Volkwein, Pittsburgh, Pa.

[73] Assignee: Secretary of the Interior, Washington, D.C.

[21] Appl. No.: 245,236

[22] Filed: May 17, 1994

Related U.S. Application Data

[63] Continuation of Ser. No. 540,598, Jun. 20, 1990, abandoned.

[51] Int. Cl.$^6$ .......................... C12Q 1/04; C12Q 1/24; C12P 5/02
[52] U.S. Cl. ........................................ 435/34; 435/42; 435/167; 435/254.4
[58] Field of Search ................ 435/34, 42, 167, 254.4

[56] References Cited

U.S. PATENT DOCUMENTS

| | | |
|---|---|---|
| Re. 31,347 | 8/1983 | Reijonen et al. ............... 435/167 |
| 1,990,523 | 2/1935 | Buswell et al. ................. 435/167 |
| 3,640,846 | 2/1972 | Johnson .......................... 435/167 |
| 3,826,308 | 7/1974 | Compere-Whitney ......... 435/166 |
| 4,316,961 | 2/1982 | Klass ............................... 435/167 |
| 4,329,428 | 5/1982 | Ghosh et al. ................... 435/167 |
| 4,424,064 | 1/1984 | Klass et al. ..................... 435/167 |
| 4,579,562 | 4/1986 | Tarman et al. .................. 435/167 |
| 4,666,605 | 5/1987 | Minami et al. .................. 435/167 |
| 4,826,769 | 5/1989 | Menger ............................ 435/167 |
| 4,845,034 | 7/1989 | Menger et al. .................. 435/167 |

OTHER PUBLICATIONS

Derwent ABS 91-021958/03 (Dec. 18, 1990) Volkhein ABS US7540598.

*Primary Examiner*—Herbert J. Lilling
*Attorney, Agent, or Firm*—Larson and Taylor

[57] ABSTRACT

A method and apparatus are provided for the in situ biological conversion of coal to methane comprising culturing on a coal-containing substrate a consortium of microorganisms capable of degrading the coal into methane under suitable conditions. This consortium of microorganisms can be obtained from an underground cavity such as an abandoned mine which underwent a change from being supplied with sewage to where no sewage was present, since these conditions have favored the development of microorganisms capable of using coal as a carbon source and converting coal to methane. The consortium of microorganisms obtained from such abandoned coal mines can be isolated and introduced to hard-to-reach coal-containing substrates which lack such microorganisms and which would otherwise remain unrecoverable. The present invention comprises a significant advantage in that useable energy can be obtained from a number of abandoned mine sites or other areas wherein coal is no longer being recovered, and such energy can be obtained in a safe, efficient, and inexpensive manner.

19 Claims, 1 Drawing Sheet

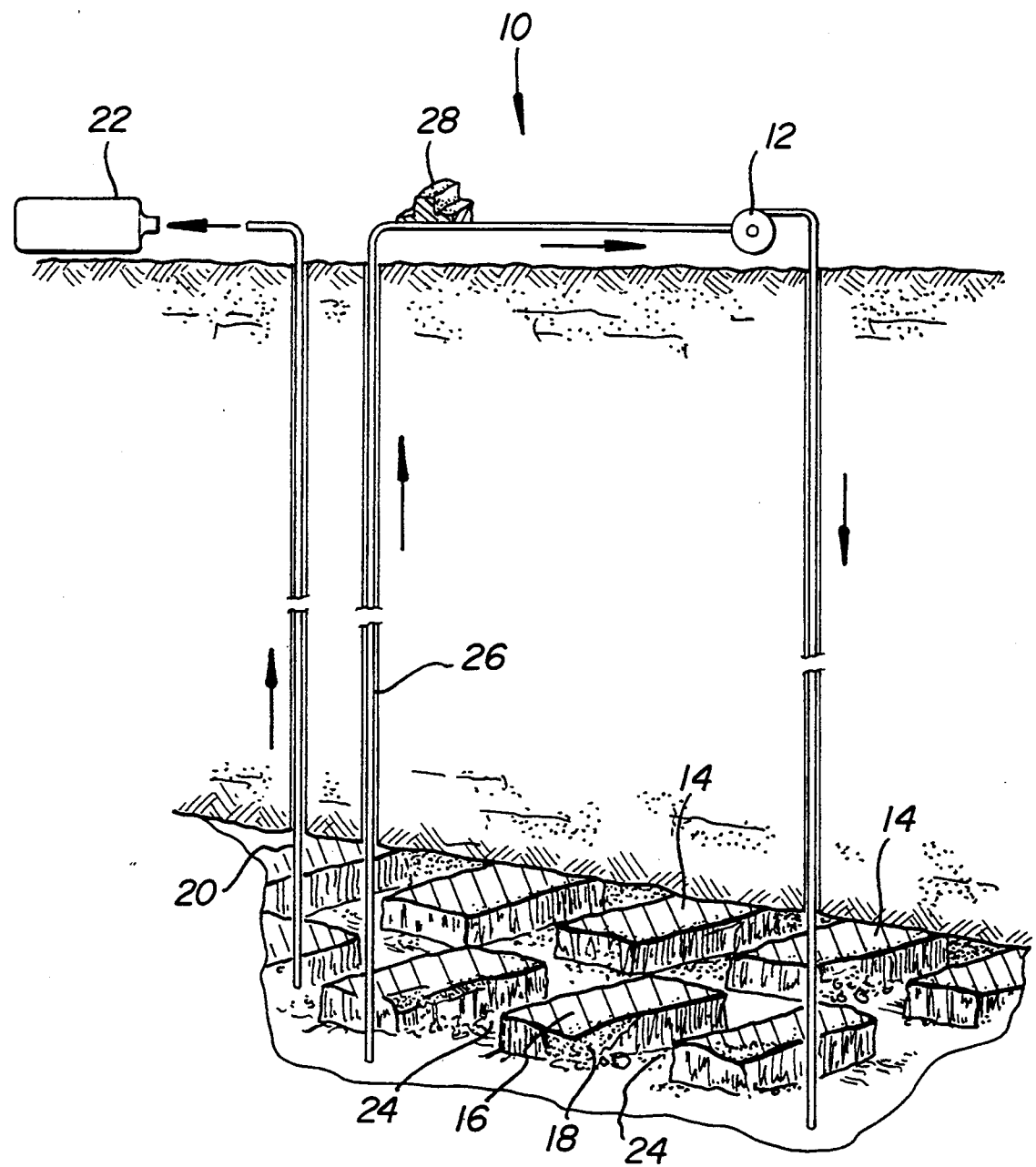

METHOD FOR IN SITU BIOLOGICAL CONVERSION OF COAL TO METHANE

This application is a continuation of application Ser. No. 07/540,598, filed Jun. 20, 1990, now abandoned.

FIELD OF THE INVENTION

The invention relates in general to a method for biologically converting coal to methane, and in particular to a method and apparatus for culturing in situ on a coal-containing substrate a consortium of microorganisms capable of degrading coal into methane under suitable anaerobic conditions.

BACKGROUND OF THE INVENTION

Over the past several years, advances in the field of biotechnology have resulted in significant advances in areas such as pharmaceuticals, agriculture, treatment of toxic waste, bioleaching of precious or toxic metals, and removal of sulfur from coal. Further examples of uses of biotechnology with regard to coal can be found in Couch, "Biotechnology and Coal", *IEA Coal, Research* (1987).

The inability to recover coal that remains after a mining operation is completed is an issue that has received much attention over the past few years. The major reason for this is that over the past fifty years, it is estimated that in the U.S. alone, over 168 quadrillion ($10^{15}$) BTU's of unrecovered coal have remained unexploited after conventional mining, much of this in the form of unrecoverable coal gobs. For each year of mining that passes, roughly an additional three quadrillion BTU's of energy resources remain unrecovered. Most often, chemical and mechanical means have been used in attempts to recover the remaining coal, but these methods suffer from various drawbacks which often make them economically unfeasible.

More recently, some attempts have been made to develop biological methods to convert coal to methane. However, these attempts have not been directed to degrading coal in situ, and thus cannot be applied to recovering the vast amounts of coal that remain following a completed mining operation.

Additionally, most recent attempts in the area of biological conversion of coal have been directed to degrading low-rank softer coals, such as lignite, which are less desirable and have a higher moisture content. Examples of such attempts include work by groups such as Arctech, Inc. (see Barik et al, *Biological Conversion of Low-Rank Coals,* Arctech, Inc., Alexandria, Va.) and Houston Lighting and Power (see Leushner et al, in 13*th Biennial Lignite Symposium on Technology and Use of Low Rank Coals,* pp. 216–228), who have both disclosed conversion of low rank lignite coal to methane via single step or two step processes involving anaerobic microbes. However, tests involving these microbes on harder, higher rank coals were unsuccessful. These processes also suffer from the drawbacks that because of the slow growth of the anaerobic microorganisms, extremely large reaction vessels are required to produce economic quantities of the desired product, and careful attention must be paid to the environmental conditions for the survival of these organisms. There thus exists the need to develop biological methods of converting high rank coals to methane which can be used in situ in an economical and effective way.

In the patent arts, there has been disclosed the use of large reaction chambers for the gasification of lignite under a primarily two step process as disclosed in U.S. Pat. Nos. 4,845,034 (Menger et al) and 4,826,769 (Menger). These patents relate to a method for degrading lignite coal placed in a subterranean cavity by inoculating the lignite with a culture of microorganisms and allowing the microorganisms to grow on the substrate placed in the cavity, followed by recovery of the biochemical products formed thereby. As in the above described methods, however, the Menger patents suffer from several drawbacks and additionally cannot be used to recover methane from higher rank coals in situ. Among these drawbacks, the Menger method requires that the coal be presolubilized using very high temperatures and alkali solutions. Further, the use of the underground cavity is strictly as a bioreactor and not as a source of coal feedstock. As a result, the coal acted on must be provided to the underground cavity, and coal is not treated in situ. This method requires that surface processing of the substrate materials must be undergone before the reaction can proceed, and this includes finely grinding lignite coal, and making it into a slurry which is then pumped into the subterranean bioreactor. The method also suffers because of its requirement for fast turnover rates on the order of days to achieve an economic operation, and this is difficult because of the slow growth of the anaerobic microorganisms and the achieving of the bioconversion of the lignite coal which is lengthy as well.

It is thus highly desirable to develop a system by which high rank coals such as bituminous coals can be converted into methane using biological methods. It is also highly desirable that a method be found by which an in situ conversion of coals which would otherwise go unutilized be found. This is extremely important because a great deal of coal still remains from abandoned mines or other unminable coal seams which, if converted to methane, could become an extremely important source of energy.

SUMMARY OF THE INVENTION

A previously unknown consortium of microorganisms has been discovered and isolated and can be used in the in situ biological conversion of higher rank coals to methane. The method of the present invention comprises culturing on a coal-containing substrate this consortium of microorganisms under conditions which are suitable for allowing the biological conversion of coal to methane. This consortium of microorganisms is obtained from areas such as an abandoned underground mine where specific conditions have favored the development of microorganisms which are capable of using coal as a carbon source. The method of the present invention can be carried out by culturing those microorganisms already located in the underground mines where conditions have favored their development, or 2by isolating the consortium and inoculating it onto any coal-containing substrate where the conditions can be adjusted so as to favor the growth of the methanogenic consortium of microorganisms of the invention. An apparatus for carrying out the method of the present invention is also provided.

The present method and apparatus is extremely advantageous in that it allows for the in situ conversion of previously unusable coal substrates into usable methane in a highly efficient and economic manner heretofore unobtainable.

BRIEF DESCRIPTION OF THE DRAWING FIGURE

The drawing FIGURE is a schematic view of an apparatus for carrying out the method of the present invention.

DETAILED DESCRIPTION OF THE PREFERRED EMBODIMENTS

The method of the present invention relates to the isolation and use of a consortium of anaerobic microorganisms which can be used to degrade coal into methane under specific conditions. These microorganisms have developed over the years particularly in sealed underground cavities where conditions have favored the development of microbial populations which were able to use coal as a carbon source. In particular, in many abandoned mine sites, the past practice of surface homeowners in the vicinity of the mines was to dispose household sewage into those mines when abandoned. This procedure had the effect of introducing a nutritional substrate and inocula for gaseous producing organisms. At the same time, entrances to the old mines continued to subside or be sealed creating an anaerobic atmosphere and leading to the development of methane-producing anaerobic bacteria. Subsequently, installation of sewers into the area and the prohibition of dumping sewage into the mines removed this sewage as a source of carbon for the microorganisms present. As a result, the methane-producing microorganisms had to adapt from the sewage substrate to the coal substrate present in the mines as their carbon energy source. These specific conditions thus produced organisms capable of degrading coal to methane. It is thus expected that where these conditions exist (sewage providing a combination of nutrients and inoculant, temperature around 90°-100° F., and an anaerobic atmosphere, followed by a lengthy weaning period of at least several decades during which the sewage is eliminated from the coal-containing environment), it is expected that the development of methanogenic anaerobic microorganisms adapted to use coal as their primary carbon source will take place.

Accordingly, a consortium of anaerobic obligate or facultative chemoorganotrophic microorganisms has been isolated from a mine site abandoned over 75 years ago, the former Lower Walton Mine in Pennsylvania. Sediment samples obtained from this mine were cultured on medium salts, and additionally in some cases a supply of ground Pittsburgh seam coal. After several weeks of incubation, it was observed that gas production from the sediment sample cultured with coal had a significant content (about 5 mole percent) of methane and about 18 mole percent of carbon dioxide. It is clear that the sediment sample isolated from this mine known as LWM1 is thus capable of degrading coal into methane. The sediment sample containing a consortium of microorganisms known as LWM1 which is capable of converting coal into methane has been deposited at the American Type Culture Collection of Rockville, Md. and has been accorded Accession No. 55237. This consortium can thus be used in a method of biologically converting coal in situ to methane by culturing the consortium on a coal containing substrate under conditions suitable for promoting the growth of these microorganisms.

In studies of two other abandoned mine sites similar to the former Lower Walton Mine wherein conditions had undergone a change from a point where a nutrient source such as sewage was present to a point where that nutrient source was absent, sediment samples taken from these sites have also been shown to contain a consortium of microorganisms capable of converting coal to methane. As would be recognized by one of ordinary skill in the art, one should expect to find a consortium of microorganisms capable of converting coal to methane in virtually all of the previously unstudied abandoned mine sites and other sealed underground cavities which have undergone the change in conditions as set forth above. In addition, when such underground sites are located, as will also be recognized by one of ordinary skill in the art, microorganism consortia capable of converting coal to methane can be located using well known conventional screening techniques that are commonly used in this field.

The consortium of microorganisms isolated in accordance with the present invention is further advantageous in that it has been found capable of degrading high rank coals to methane, a step that previous biological methods in this field have failed to accomplish. In particular, the consortium can be used in the in situ conversion of high rank coals such as bituminous and sub-bituminous coals. It is also contemplated that the method of the invention can also be used to convert lower rank coals to methane if so desired. These lower rank coals would include lignite and leonardite coals.

In the preferred embodiment of the present invention, a solution containing the consortium of microorganisms as obtained above along with suitable nutrients will be pumped onto a coal-containing substrate such as abandoned mine or a coal seam. If the area including the coal-containing substrate is one that because of conditions as discussed above has present its own populations of methane-producing microorganisms, then the conversion of coal to methane can be carried out by pumping a nutrient solution into the region of the coal-containing substrate and adjusting the conditions so that they favor the conversion of coal into methane by the microorganisms.

Ideally, the culturing of organisms in accordance with the present invention will be carried out in an abandoned mine or other underground cavity or coal seam under anaerobic conditions. It is particularly preferred that the microorganisms are cultured in a liquid phase in contact with the coal-containing substrate being converted to methane. Conditions should be adjusted so that oxygen concentrations are less than about 0.5 percent (most preferably less than 0.1 percent), a temperature of from about 45 to about 120° F. (most preferably about 90°-100° F.), a pH of between about 3.5 and 8.0 (most preferably 6.5-7.0), and a pressure of less than about 15 atmospheres (most preferably less than about 10 atmospheres). The source of nutrients which will be added in order to favor the growth of the microorganisms and conversion of the coal to methane generally will include nitrogen, phosphorus, potassium, sulfur, B vitamins, and trace minerals, and most preferably, all of these will be combined in solution and used as the nutrient source.

An apparatus suitable for carrying out the method of the present invention is observed in the drawing FIGURE. The apparatus 10 consists of a pump 12 which is used to introduce a solution containing nutrients into an underground cavity such as an abandoned mine. Pump 12 may also be used to provide the inoculum containing the consortium of microorganisms capable of degrading coal into methane which will be introduced into the coal-containing substrate. In the drawing FIGURE, pillars of coal 14 that are left behind after the mine has been abandoned contain previously unrecovered coal which can be converted to methane by use of the method of the present invention. Over time, certain pillars 16 have crumbled significantly, which exposes fresh coal surfaces 18 that can be microbially degraded by the microorganisms of the present invention. When the solution and inoculum is pumped into the mine, the coal will be converted into methane and product gas will accumulate at the high points in the mine. Therefore, the methane gas produced from the coal can be recovered by means of a gaseous pipe 20 leading from the mine ceiling to a recovery tank 22 on the surface. In general, the areas between pillars of coal 24 will be filled with the nutrient-bearing liquid solution pumped into the mine. The liquid used is preferably water or a suitable organic solvent. An additional feature that may be added to this apparatus is a second pipe system 26 used to extract spent liquid. This piping system can cause the liquid underground to circulate around the pillars, and can also be used to measure the conditions of the underground environment when the liquid is pumped out of the mine and monitored at point 28. Any imbalance of essential conditions that are determined at this point may be adjusted by addition of appropriate chemicals or nutrients before the liquid is pumped back into the mine. The recovered methane or other gaseous products may be separated on site or piped to a central location for separation and purification.

A significant advantage of the present invention is that the slow conversion of coal to methane by the microorganisms which normally hinders other methods of producing methane from coal is not a problem in this case. The present invention overcomes these drawbacks by not using a central plant and thus avoiding large capital costs. The method is such that the slow processes of anaerobic organisms are not significant. The system is designed so that large initial costs and continuing operation costs are minimized, thus methane can be accumulated economically over a course of months or years. In most areas of the world where coal is found, oil and natural gas are also present. This fact usually means that there is an already present infrastructure of gas pipelines that may be employed into an apparatus capable of carrying out the present invention. The invention contemplates a decentralized network of production facilities, using boreholes and small pumping-/fertilizing stations which may be connected to the existing pipelines. Additionally, the space available for gas production will be spread out over many square miles of abandoned underground workings. This means that reaction times, orders of magnitude less than those of the prior art, will still produce economic quantities of natural gas.

Another particular advantage of the present invention is that it can be specifically used to degrade high rank coals, such as bituminous coals, which have not previously been biologically converted to methane. Previously used methods., such as those described in U.S. Pat. Nos. 4,845,034 and 4,826,769, have only been able to operate on lower rank coals such as lignite, and even then require large temperatures and an alkali solution in order to presolubilize the coal which is then converted to gaseous product. The present invention does not require presolubilization of the coal, yet is able to degrade the hard coals which can be gasified and recovered as methane gas.

The present invention will thus comprise an extremely rewarding method of utilizing previously unrecovered coal so as to be useful as an energy source. This has been a major problem in the U.S. in that the large number of underground coal mines only typically remove no more than about 50–75 percent of the seams of coal mined. In addition to coal that cannot be reached, some coal must be left in place to support the roof while the miners remove the machinery and exit the mine when a mining procedure is completed. Heretofore, no techniques existed to remove this remaining coal from the abandoned mines, and thus this coal remained unutilized. With the present invention, this residual coal is seeded with liquid nutrients and an inoculant of microorganisms which is capable of converting the coal into methane, and this method allows recovery of methane which then can be utilized as an energy source.

Abandoned mines and other underground cavities will provide an ideal environment for biogasification of coal remaining in those cavities. Such mines frequently contain water and in many cases are completely flooded with water. Very often, because of the removal of most of the coal originally, the permeability through the deposit resulting from the old tunnels will be good. Over time, pressure from the roof often causes the pillars of remaining coal to slowly collapse and therefore expose fresh coal surfaces which can be treated using the method of the present invention. The important step in addition to the providing of a consortium of microorganisms capable of converting the coal to methane, is the provisions of nutrients which allow the microorganisms to thrive and grow on the coal-containing substrate.

Previously, no microorganisms have been shown which can produce methane from a substrate of high rank coals such as bituminous coal. The present invention provides an isolation procedure for obtaining a consortium of microorganisms which can degrade such high rank coals. At present, investigations reveal that there are several different microorganisms involved in the consortium, but it is not presently known exactly what types of microorganisms are present. It is clear that the consortium consists of organisms capable of degrading complex polynuclear aromatic compounds and heterocyclic organic structures to simple acids, organic acid degrading microorganisms which yield formate and acetate, and finally, the methane-producing microorganisms. The gases produced by the degrading of coal by these microorganisms are essentially comprised of methane and carbon dioxide.

The abandoned mine sites or other underground cavities where conditions are as described above and which are likely to contain microorganisms capable of converting coal to methane will thus be located easily by one skilled in the art. When such a suitable mine site or underground cavity is located, the apparatus of the present invention can be installed, and the nutrient solution and/or a solution including microorganisms and nutrients can be pumped into the abandoned mine. Further, through use of a suitable solution or other means, temperature and pressure can also be adjusted so that the conditions favor the conversion of coal to methane. It is preferred that a gas recovery system be established by first surveying the abandoned mine, determining the dip and strike of the seam, and boring gas recovery holes into the high points of the seam. By this procedure, the gaseous product phase will self-separate from the liquid/solid (nutrients/substrate) phase, and the methane produced by the biological conversion of the coal can be recovered over the course of several months or several years.

Another indication that a proper site is found wherein microorganisms capable of converting coal to methane are present, is the presence of methane which is not usually found in outcrop coal above the water table. In mines checked where it was thought that such microorganisms might be present, mine gas levels were measured during thermal and barometric pressure changes at a surface access point to the abandoned mine. During periods of maximum outgassing, an analysis showed a small amount of methane in addition to carbon dioxide, oxygen, and nitrogen. Since methane was not observed during periods of minimal outgassing, the observed methane was most likely originating from deeper areas in the mine. The areas of the mine which are governed by a strict anaerobic atmosphere and which are producing trace amounts of methane evidence the existence of microorganisms producing methane from coal.

It is contemplated by the present invention that the use of other coal-containing substrates, such as unmined coal seams, can be used for in situ bioconversion of coal to methane. There are many cases where for various reasons, coal seams are unminable by current technology. In these cases, the permeability of the seam could be enhanced by fracturing the coal in order to make the coal-containing substrate amenable to the present invention. The fracturing could be accomplished by explosives or hydrofracturing the coal in manner similar to techniques that the oil industry uses to increase the permeability of oil-bearing formations. Once made amenable to the present invention, nutrients and inocula containing the consortium of microorganisms of the invention can be added to coal-containing substrate, and the extraction of the produced methane would take place as described above. The present invention is also advantageous in that certain seams of coal that are minable by current techniques still do not meet the sulfur or ash requirements of the market. In these cases, the seams could be prepared for the present method by enhancing the permeability via conventional mining techniques or other fracturing methods described above, and then these seams would be amenable to the bioconversion techniques discussed above which ultimately produce clean energy.

It is also possible to use as the source of nutrients for the present invention treated or untreated sewage waste. Since the users of this invention would have an economic incentive to conserve the cost of the nutritional supplement that must be provided, the environmental problems of treating sewage in this manner could be handled so that sewage could be employed. Accordingly, the natural influx of water into the mine, and subsequent drainage from the mine would need to be suitably controlled.

The present invention thus provides a method, apparatus, and a consortium of microorganisms that can be used in the conversion of coal into methane, particularly with regard to previously under-utilized high rank coals in abandoned mines which can be converted to methane in situ in an efficient and economic manner. The consortium of microorganisms isolated and identified above can be used in any suitable situation wherein coal is to be converted into methane and conditions can be adjusted so that they are favorable to the growth of the microorganisms and to the biological conversion process that is carried out by those organisms.

The following example is presented as illustrative of the present invention and is not intended in any way to limit its scope:

EXAMPLE 1

Anaerobic sediment samples were obtained from the former Lower Walter Mine in Pennsylvania, and aliquots from the samples were cultured on medium salts and other ingredients. The preferred cultured medium for the samples contained trace minerals and metals, B vitamins, yeast extract, resazurin, and sodium salts, as indicated in Table I. The sediment samples were cultured in this medium and in other mediums containing benzoate, acetate, salts only, Pittsburgh seam coal, and a control containing no medium salts. After 48 days of incubation, gas production from the sediment samples was monitored. From the sediment sample known as LWM1 which was cultured with the coal, 4.7 mole percent of methane and 18.3 mole percent of carbon dioxide were detected. Both acetate and benzoate produced methane at 38.4 and 3.5, respectively. The control sample with no media produced no methane. The tests indicated that the sample identified as LWM1 contained a consortium of microorganisms capable of converting coal into methane and carbon dioxide. It is contemplated that skilled practitioners using isolation techniques well known in the art should be able to isolate similar microorganisms which have adapted to degrading specific coals.

TABLE I

| Material in Distilled $H_2O$ | | Volume or Weight Percent |
| --- | --- | --- |
| Pfennings mineral per liter distilled $H_2O$ | | 5.0 |
| $KH_2PO_4$ | 10 mg | |
| $MgCl_2.5H_2O$ | 6.6 g | |
| NaCl | 8.0 g | |
| $NH_4Cl$ | 8.0 g | |
| $CaCl_2.2H_2O$ | 1.0 g | |
| Pfennings Trace metal per liter distilled $H_2O$ | | 0.1 |
| $ZnSO_4.7H_2O$ | 0.1 g | |
| $MnCl_2.4H_2O$ | 0.03 g | |
| $H_3BO_3$ | 0.3 g | |
| $COCl_2.6H_2O$ | 0.2 g | |
| $CuCl_2.2H_2O$ | 0.01 g | |
| $NiCl_2.6H_2O$ | 0.02 g | |
| $Na_2MoO_4.2H_2O$ | 0.03 g | |
| $FeCl_2.4H_2O$ | 1.5 g | |
| B-Vitamins per liter distilled $H_2O$ | | 0.5 |
| Nicotinic acid | 20 mg | |
| Cyanocobalamine | 20 mg | |
| Thiamin | 10 mg | |
| p-aminobenzoic acid | 10 mg | |
| pyridoxin | 50 mg | |
| Panothenic acid | 5 mg | |
| Resazurin | | 0.1 |
| Yeast extract | | 0.2 |
| $NaHCO_3$ | | 0.35 |
| $Na_2SeO_3.5H_2O$ | | 0.1 |
| $Na_2S$ | | 2.0 |

What is claimed is:

1. A method of biological conversion of in situ coal to methane without rigorous conditions or pretreatment steps, said method comprising the steps of:
    (a) locating an underground cavity where conditions underwent a change from a point where a nutrient source was present to a point where the nutrient source was absent and the growth of microorganisms capable of producing methane from coal was promoted;

(b) recovering sediment samples from said cavity;

(c) testing the recovered samples to determine which samples contain a consortium of anaerobic obligate or facultative chemoorganotrophic microorganisms capable of converting coal to methane;

(d) selecting those samples that contain a consortium of anaerobic obligate or facultative chemoorganotrophic microorganisms capable of converting coal to methane;

(e) adding the selected consortium of microorganisms to a coal-containing substrate; and (f) culturing the consortium of microorganisms on the coal-containing substrate so that coal is converted to methane.

2. A method according to claim 1 wherein the culturing is carried out under anaerobic conditions.

3. A method according to claim 1 wherein the underground cavity comprises an abandoned mine.

4. A method according to claim 1 further comprising the step of recovering the methane produced by the in situ biological conversion of coal.

5. A method according to claim 1 wherein the consortium of microorganisms is added to the coal-containing substrate by pumping a solution containing the consortium and nutrients into the region including the coal-containing substrate.

6. A method according to claim 5 wherein the solution containing the consortium and nutrients comprises sewage to which the consortium has been added.

7. A method according to claim 1 wherein the culturing conditions comprise:
   a) an $O_2$ concentration of less than about 0.5%;
   b) a temperature of from about 45° to 120° F.;
   c) a pH of between 3.5 and 8.0; and
   d) a pressure of less than about 15 atmospheres.

8. A method according to claim 1 wherein the culturing conditions comprise:
   a) an $O_2$ concentration of less than about 0.1%;
   b) a temperature of from about 90° to about 100° F.;
   c) a pH of between about 6.5 and 7.0; and
   d) a pressure of less than about 10 atmospheres.

9. A method according to claim 1 wherein the microorganisms are cultured in a liquid phase which is contacted with the coal-containing substrate.

10. A method according to claim 1 wherein the culturing conditions include the addition of nutrients which favor the growth of the selected consortium of microorganisms and the biological conversion of coal to methane.

11. A method according to claim 10 wherein the nutrients are selected from the group consisting of nitrogen, phosphorus, potassium, sulfur, B vitamins, trace minerals, and combinations of these nutrients.

12. A method according to claim 1 wherein the coal-containing substrate is located in a sealed underground cavity.

13. A method according to claim 1 wherein the coal-containing substrate is located in an abandoned coal mine.

14. A method according to claim 1 wherein the coal-containing substrate is a coal seam.

15. A method according to claim 1 wherein the coal converted to methane is a high-rank coal.

16. A method according to claim 1 wherein the coal converted to methane is bituminous coal.

17. A method according to claim 1 wherein the coal converted to methane is selected from the group consisting of low-rank coals, sub-bituminous coals, lignite coals, and leonardite coals.

18. A method according to claim 1 wherein the consortium of microorganisms comprises a consortium which is identified as LWM1 and which is deposited at the American Type Culture Collection, bearing Accession No. 55237.

19. A method according to claim 1 wherein the microorganisms capable of converting coal to methane comprise microorganisms capable of degrading complex polynuclear aromatic compounds and heterocyclic organic structures to simple acids, organic acid-degrading microorganisms which yield formate and acetate, and methane-producing microorganisms capable of producing methane from organic acids.

* * * * *